United States Patent
Lui et al.

(10) Patent No.: US 6,645,961 B1
(45) Date of Patent: Nov. 11, 2003

(54) DRY GRANULATION FORMULATION FOR AN HIV PROTEASE INHIBITOR

(75) Inventors: Chung Y. Lui, Lansdale, PA (US); Drazen Ostovic, Lansdale, PA (US); Ashok V. Katdare, Norristown, PA (US); Christine Stelmach, Tinton Falls, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/045,885

(22) Filed: Mar. 4, 1998

Related U.S. Application Data

(60) Provisional application No. 60/040,158, filed on Mar. 7, 1997.

(51) Int. Cl.$^7$ ................ A61K 31/535; A61K 31/495; A61K 31/47
(52) U.S. Cl. ................ 514/231.5; 514/252; 514/255; 514/311
(58) Field of Search ............... 514/231.5, 252, 514/255, 311

(56) References Cited

U.S. PATENT DOCUMENTS

| | | | |
|---|---|---|---|
| 5,169,952 A | 12/1992 | Askin et al. | 544/137 |
| 5,413,999 A * | 5/1995 | Vacca et al. | 514/231.5 |
| 5,420,353 A | 5/1995 | Verhoeven et al. | 564/399 |
| 5,463,067 A | 10/1995 | Askin et al. | 548/113 |
| 5,491,238 A | 2/1996 | Askin et al. | 546/270 |
| 5,496,948 A | 3/1996 | Askin et al. | 544/368 |

FOREIGN PATENT DOCUMENTS

EP  0 541 168 A1  12/1993  ......... C07D/217/26

OTHER PUBLICATIONS

Remington's Pharm Sci, 17$^{th}$ Ed Gennaro et al ed pp 1314, 1315, 1604–1606 & 1613, 1985.*

Lachman et al., "The Theory and Practice of Industrial Pharmacy", 1986, Lea & Febiger, pp. 325–327.

Physician's Desk Reference, "Crixivan Capsules", (1997), pp. 1670–1673.

* cited by examiner

Primary Examiner—Russell Travers
(74) Attorney, Agent, or Firm—Kenneth R. Walton; Valerie J. Camara; Melvin Winokur

(57) ABSTRACT

This invention relates to a dry granulation capsule formulation of the HIV protease inhibitor, indinavir sulfate, which is useful in the treatment of AIDS, ARC or HIV infection. Processes for making the oral formulation are also disclosed.

19 Claims, No Drawings

DRY GRANULATION FORMULATION FOR AN HIV PROTEASE INHIBITOR

This application claims the benefit of U.S. Provisional Application No. 60/040,158, filed Mar. 7, 1997.

FIELD OF THE INVENTION

The present invention relates to solid dosage formulations, and process for manufacture, of an HIV protease inhibitor. More specifically, the invention relates to a dry granulation formulation of the HIV protease inhibitor, indinavir.

BACKGROUND OF THE INVENTION

The pharmaceutical industry employs various methods for compounding pharmaceutical agents in oral formulations. In particular, wet granulation is one of the more prevalent methods for preparing tablets and/or capsules. When tablet (capsule) ingredients are sensitive to moisture or are unable to withstand elevated temperatures during drying, and when tablet (capsule) ingredients have sufficient inherent binding or cohesive properties, slugging may be used to form granules. This method is also known as dry granulation. The encapsulation of medicinal agents provides a popular alternative to the tablet for administering drugs. The hard gelatin capsule, available in a large variety of sizes, consists of two sections one slipping over the other to completely surround the drug formulation.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. Recently, a number of HIV protease inhibitor compounds have been disclosed as being useful in the treatment of infection by HIV and in the treatment of AIDS. These HIV protease inhibitor compounds and their utility in treating HIV and AIDS is described in U.S. Pat. No. 5,413,999 and EP 541,168, published May 12, 1993. More particularly, the compound disclosed and referred to as "Compound J" in U.S. Pat. No. 5,413,999 and EP 541,168, is a potent inhibitor of HIV protease and is useful in the treatment of infection by HIV and in the treatment of AIDS or ARC (AIDS related complex), without significant side effects or toxicity.

Compound J

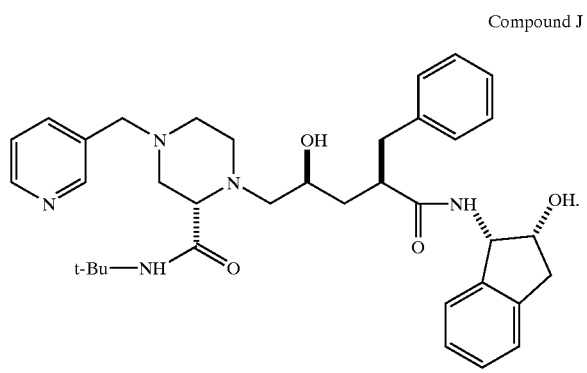

Compound J, i.e., N-(2(R)-hydroxy-1(S)-indanyl)-2(R)-phenylmethyl-4-(S)-hydroxy-5-(1-(4-(3-pyridylmethyl)-2(S)-N'-(t-butylcarboxamido)-piperazinyl))-pentaneamide, now also known as indinavir, is prepared according to the procedure of Example 15 in U.S. Pat. No. 5,413,999 or according to the Vocesses disclosed in U.S. Pat. Nos. 5,420, 353; 5,169,952; 5,463,067; 5,496,948; 5,491,238. The sulfate salt of Compound J (more specifically, the sulfate salt ethanolate) is currently marketed as CRIXVAN® (trademark of Merck & Co. Inc.), i.e., indinavir sulfate.

Devising an oral formulation of indinavir, in particular, indinavir sulfate, proved problematic for a number of reasons. The daily dose of indinavir sulfate is quite high, i.e., 2.4 g per day; therefore the formulation should contain a minimum number of excipients. Moreover, since indinavir sulfate does not possess good compaction properties, an excipient with good compaction properties was necessary. Additionally, indinavir sulfate is very moisture sensitive making formulation difficult. Furthermore, many HIV protease inhibitors, including indinavir sulfate, have bitter and unpleasant taste.

The present invention now provides a dry granulation formulation of indinavir sulfate and process therefore which solves all of the problems discussed above.

SUMMARY OF THE INVENTION

The present invention provides a pharmaceutical composition which comprises by weight, about 50 to 90% by weight of an active ingredient which is indinavir, or a pharmaceutically acceptable salt thereof,.about 10 to 50% by weight of an excipient and about 0.5 to 2% by weight of a lubricant. Preferably, the active ingredient is indinavir sulfate. More preferably, the active ingredient is indinavir sulfate, the excipient is selected from anhydrous lactose, low moisture microcrystalline cellulose or anhydrous calcium phosphate dibasic, and the lubricant is selected from magnesium stearate, sodium lauryl sulfate, sodium stearyl fumarate or hydrogenated vegetable oil. Most preferably, the active ingredient is indinavir sulfate, the excipient is anhydrous lactose and the lubricant is magnesium stearate.

In one embodiment of the invention is the pharmaceutical composition which comprises by weight, about 70 to 80% by weight indinavir sulfate, about 20 to 30% by weight of the excipient and about 0.8% to 1.5% by weight of the lubricant. Preferably, the excipient is selected from anhydrous lactose, low moisture microcrystalline cellulose or anhydrous calcium phosphate dibasic, and the lubricant is selected from magnesium stearate, sodium lauryl sulfate, sodium stearyl fumarate or hydrogenated vegetable oil; most preferably, the excipient is anhydrous lactose and the lubricant is magnesium stearate.

In a class of the invention is the pharmaceutical composition which comprises by weight, about 75 to 78% by weight indinavir sulfate, about 22 to 25% by weight anhydrous lactose and about 0.9% to 1.1% by weight magnesium stearate.

In a subclass of the invention is the pharmaceutical composition which comprises by weight, about 76% by weight indinavir sulfate, about 23% by weight anhydrous lactose and about 1% by weight magnesium stearate.

Illustrative of the invention is the pharmaceutical composition in the form of a capsule.

An illustration of the invention is a process for making a pharmaceutical composition containing an active ingredient of indinavir, or a pharmaceutically acceptable salt thereof, comprising the steps of:

(a) mixing about 50 to 90% by weight of the active ingredient with about 10 to 50% by weight of an excipient and about 0.25 to 1% by weight of a first lubricant;

(b) compacting the mix from step (a) to form compacts;

(c) milling the compacts from step (b) to form granules;

(d) lubricating the granules from step (c) with about 0.25 to 1% by weight of a second lubricant; and (e) forming the lubricated granules from step (d) into the pharmaceutical composition.

In a preferred embodiment of this process, the pharmaceutical composition is formed by encapsulating the lubricated granules from step (d) to form a capsule.

Exemplifying the invention is the process further comprising, the steps of:

(f) sieving the compacts discharged from the compactor in step (b) prior to milling;

(g) collecting the uncompacted material from step (f); and (h) recycling the collected material back to the compactor.

An example of the invention is the process wherein the active ingredient is indinavir sulfate.

Further illustrating the invention is the process wherein the excipient is selected from anhydrous lactose, low moisture microcrystalline cellulose or anhydrous calcium phosphate dibasic, and the first and second lubricants are each independently selected from magnesium stearate, sodium lauryl sulfate, sodium stearyl fumarate or hydrogenated vegetable oil. Preferably, the first and second lubricant are the same. Most preferably, the first and second lubricants are both magnesium stearate and the excipient is anhydrous lactose.

Further exemplifying the invention is the process wherein the capsule contains about 70 to 80% by weight indinavir sulfate, about 20 to 30% by weight anhydrous lactose and about 0.8% to 1.5% by weight magnesium stearate; preferably, about 75 to 78% by weight indinavir sulfate, about 22 to 25% by weight anhydrous lactose and about 0.9% to 1.1% by weight magnesium stearate.

More particularly illustrating the invention is the process comprising the steps of:

(a) mixing about 76% by weight indinavir sulfate, with about 23% by weight anhydrous lactose and about 0.5% by weight magnesium stearate;

(b) compacting the mix from step (a) in a roller compactor to form compacts;

(c) milling the compacts from step (b) to form granules;

(d) lubricating the granules from step (c) with about 0.5% by weight magnesium stearate; and (e) encapsulating the lubricated granules from step (d) to form the capsule.

More specifically exemplifying the invention is the process comprising the steps of:

(a) mixing about 70 to 80% by weight indinavir sulfate, preferably about 76% by weight indinavir sulfate, with about 20 to 30% by weight of the excipient, preferably about 23% by weight of the excipient, and about 0.4 to 0.75% by weight of the first lubricant, preferably about 0.5% by weight of the first lubricant, in a ribbon mixer for approximately ten minutes at 20 rpm;

(b) compacting the mix from step (a) in a roller compactor at four to ten tons force to form compacts;

(c) milling the compacts from step (b) using a 0.062 inch screen at a speed of 2000 to 2500 rpm to form granules;

(d) lubricating the granules from step (c) with about 0.4 to 0.75% by weight of the second lubricant, preferably about 0.5% by weight of the second lubricant; and (e) encapsulating the lubricated granules from step (d) to form the capsule.

Preferably, the excipient is anhydrous lactose, and the first and second lubricants are magnesium stearate.

More specifically illustrating the invention is the process comprising the steps of:

(a) mixing about 75 to 78% by weight indinavir sulfate, preferably about 76% by weight indinavir sulfate, with about 22 to 25% by weight anhydrous lactose, preferably about 23% by weight anhydrous lactose, and about 0.45 to 0.55% by weight magnesium stearate, preferably about 0.5% by weight magnesium stearate, in a ten cubic foot ribbon mixer for approximately ten minutes at 20 rpm for a total of approximately 200 revolutions;

(b) compacting the mix from step (a) in a roller compactor at four to ten tons force at a speed of 7 to 15 rpm and a feed speed of 10 to 60 rpm to form compacts;

(c) milling the compacts from step (b) in a CoMil® using a 0.062 inch screen at a speed of 2000 to 2500 rpm to form granules;

(d) lubricating the granules from step (c) with about 0.45 to 0.55% by weight magnesium stearate, preferably about 0.5% by weight magnesium stearate, in a ten cubic foot ribbon mixer for approximately five minutes at 20 rpm for a total of approximately 100 revolutions; and (e) encapsulating the lubricated granules from step (d) in a Bosch GKF encapsulation machine to form the capsule.

An additional example of the invention is a pharmaceutical composition made by any of the processes described above.

Additional illustrations of the invention are methods of treating AIDS, and/or infection by HIV which comprises administering to a human in need thereof, a therapeutically effective amount of any of the pharmaceutical compositions described above.

DETAILED DESCRIPTION OF THE INVENTION

The disclosed process may be used to prepare solid dosage forms, particularly capsules, for medicinal administration. A capsule rather than tablet dosage form is preferable because hard gelatin capsules contain and taste mask the product eliminating the need to non-aqueous film coat the tablets for taste masking, thereby avoiding the use of environmentally unfriendly solvent. White opaque hard gelatin capsules of various sizes are used to encapsulate this formulation to produce different potencies as described in detail in the Examples which follow.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The term "active ingredient," as used herein includes both the free base indinavir, as well as the pharmaceutically acceptable salts thereof. In a preferred embodiment, indinavir sulfate, CRIXVAN® is used.

Preferred excepients include: anhydrous lactose, low moisture microcrystalline cellulose, and anhydrous calcium phosphate dibasic and other suitable low moisture or anhydrous diluents (see, e.g., Remington's Pharmaceutical Sciences, 18th Edition, 1990, p. 1635). Anhydrous lactose is particularly preferred.

Preferred lubricants include magnesium stearate, calcium stearate, sodium lauryl sulfate, sodium stearyl fumarate, hydrogenated vegetable oil and other known lubricants (see, e.g., Remington's Pharmaceutical Sciences, 18th Edition, 1990, pp. 1636–1637). Magnesium stearate is especially preferred. In the processes of the instant invention wherein a first lubricant and a second lubricant are employed, the first and second lubricants may be the same or different. Preferably, the first and second lubricants are the same; most preferably, both the first and second lubricants are magnesium stearate.

The pharmaceutically acceptable salts of the present invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

A direct blend process was not suitable for formulation because the preferred formulation consists of 76.2% by weight indinavir sulfate, a low bulk density material, and for the higher potencies, the low bulk density necessitated very large capsule fill volumes. Dry granulation was selected as the process of choice because of indinavir sulfate's moisture sensitivity and the desire to avoid use of organic solvents to agglomerate the powder mix. The dry granulation process of the present invention met the objectives of increasing bulk density, improving flow and providing relatively consistent granulation fill volume for encapsulation.

In general, a process for forming the capsules of the present invention involves mixing all the ingredients (e.g., active ingredient, excipient and one half the amount of lubricant) before roller compaction. In a preferred embodiment, the active ingredient is indinavir sulfate, the excipient is anhydrous lactose and the lubricant is magnesium stearate. The ingredients are mixed in any suitable mixer until a uniform mix is formed. Preferably, a ribbon mixer is employed to mix the ingredients. Most preferably, a ten cubic foot cubic mixer is utilized. After mixing, the mix is compacted using any force capable of forming a compact. Preferably, a roller compactor is used to form the compacts. Most preferably, a roller compactor at four to ten tons force is employed to form the compacts. After the compacts are generated, they are milled using any mill capable of forming suitable granules. Examples of mills which are useful for forming granules include, but are not limited to, oscillating mills and hammer mills. After milling, the remaining lubricant (e.g., magnesium stearate) is added to ensure the granulation is well lubricated before encapsulation. The lubricated granules are then encapsulated in a suitable encapsulator, preferably, a Bosch GKF encapsulator.

To ensure consistency and uniformity of granulation during scale-up, an additional step may be added to the manufacturing process, recycling of fines during roller compaction. The objective of recycling is to limit the amount of uncompacted material in the final granulation since it can adversely affect granulation flow and cause sticking during encapsulation. This was accomplished by sieving the compacts discharged from the roller compactor, collecting the uncompacted material, and recycling the uncompacted material back to the roller compactor at the end of the compaction operation. Due to the low bulk density of the indinavir sulfate and depending on the batch size, processing may consist of several sub-parts (e.g., two, three, four) up to the final lubrication step. After milling, the granules from the sub-parts are combined as a single batch, in a suitable size ribbon mixer or other suitable mixer, before final lubrication with the remaining lubricant (e.g., magnesium stearate).

The dry granulation formulation of the present invention is useful in the inhibition of HIV protease, the treatment of infection by human immunodeficiency virus (HIV) and the treatment of consequent pathological conditions such as AIDS, in adults and children. Treating AIDS or preventing or treating infection by HIV is defined as including, but not limited to, treating a wide range of states of HIV infection: AIDS, ARC, both symptomatic and asymptomatic, and actual or potential exposure to HIV. For example, the compounds of this invention are useful in treating infection by HIV after suspected past exposure to HIV by, e.g., blood transfusion, exchange of body fluids, bites, accidental needle stick, or exposure to patient blood during surgery.

The formulations of this invention can be administered to humans in the following dosage ranges. CRIXVAN® is administered orally in a dosage range between about 40 mg and about 4000 mg per day, divided into between one and four doses per day. A preferred oral adult dosage range for CRIXVAN® is between about 300 mg and about 1200 mg administered three times per day. A particularly preferred oral adult dose for CRIXVAN® is 800 mg administered three times per day. It will be understood, however, that the specific dose level and frequency of dosage for any particular patient may be varied and will depend upon a variety of factors including the activity of the specific compound employed, the metabolic stability and length of action of that compound, child vs. adult, the age, body weight, general health, sex, diet, mode and time of administration, rate of excretion, drug combination, the severity of the particular condition, and the host undergoing therapy.

The following examples are provided to further define the invention without, however, limiting the invention to the particulars of these examples.

EXAMPLE 1

I. Composition of Indinavir Sulfate Capsules

| Ingredient | mg/Capsule | | | | |
|---|---|---|---|---|---|
| Potency (as equivalent free base) | 100.0 | 200.0 | 300.0 | 400.0 | 500.0 |
| Indinavir Sulfate | 125.0 | 250.0 | 375.0 | 500.0 | 625.0 |

-continued

| Ingredient | mg/Capsule | | | | |
|---|---|---|---|---|---|
| Anhydrous Lactose NF | 37.4 | 74.8 | 112.2 | 149.6 | 187 |
| Magnesium Stearate NF | 1.63 | 3.26 | 4.89 | 6.52 | 8.15 |
| Fill Weight | 164.0 | 328.1 | 492.1 | 656.1 | 820.2 |
| Capsule Size | #3 | #1 | #0 | #00 | #00 Elongated or #000 |

II. Manufacturing Process

The ingredients (Indinavir sulfate, anhydrous lactose and half of the magnesium stearate) are blended in a suitable size ribbon mixer (e.g., a ten cubic foot mixer) and mixed for approximately 10 minutes at 20 rpm for a total of approximately 200 revolutions. The powder is then fed to a roller compactor (e.g., a Vector® roller compactor) and compacted at 4 to 10 tons force at a speed of 7 to 15 rpm and a feed speed of 10 to 60 rpm to form compacts. The uncompacted material is collected and recycled back to the roller compactor. After the roller compaction step, the compacts are milled by a CoMil® using a 0.062 inch screen at a speed of 2000 to 2500 rpm. After milling, the granules are lubricated with the remaining magnesium stearate in a suitable size ribbon mixer (e.g., a ten cubic foot mixer) for approximately five minutes at 20 rpm for a total of approximately 100 revolutions. The lubricated granules are encapsulated, preferably in a Bosch GKF encapsulation machine (e.g., Bosch GKF 1500), and the finished capsules are dedusted.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. A pharmaceutical composition which comprises about 50 to 90% by weight of an active ingredient which is indinavir sulfate, about 10 to 50% by weight of a low moisture or anhydrous excipient and about 0.5 to 2% by weight of a lubricant.

2. The pharmaceutical composition of claim 1, wherein the excipient is selected from anhydrous lactose, low moisture microcrystalline cellulose or anhydrous calcium phosphate dibasic, and the lubricant is selected from magnesium stearate, sodium lauryl sulfate, sodium stearyl fumarate or hydrogenated vegetable oil.

3. The pharmaceutical composition of claim 2 which comprises by weight, about 70 to 80% by weight indinavir sulfate, about 20 to 30% by weight of the excipient and about 0.8% to 1.5% by weight of the lubricant.

4. The pharmaceutical composition of claim 3, wherein the excipient is anhydrous lactose and the lubricant is magnesium stearate.

5. The pharmaceutical composition of claim 4 which comprises by weight, about 75 to 78% by weight indinavir sulfate, about 22 to 25% by weight anhydrous lactose and about 0.9% to 1.1% by weight magnesium stearate.

6. The pharmaceutical composition of claim 5 which comprises by weight, about 76% by weight indinavir sulfate, about 23% by weight anhydrous lactose and about 1% by weight magnesium stearate.

7. The pharmaceutical composition of claim 6 in the form of a capsule.

8. A process for making a pharmaceutical composition containing an active ingredient of indinavir sulfate, comprising the steps of:

(a) mixing about 50 to 90% by weight of the active ingredient with about 10 to 50% by weight of a low moisture or anhydrous excipient and about 0.25 to 1% by weight of a first lubricant;

(b) compacting the mix from step (a) to form compacts;

(c) milling the compacts from step (b) to form granules;

(d) lubricating the granules from step (c) with about 0.25 to 1% by weight of a second lubricant; and (e) forming the lubricated granules from step (d) into a pharmaceutical composition.

9. The process of claim 8, wherein the pharmaceutical composition is formed by encapsulating the lubricated granules from step (d) to form a capsule.

10. The process of claim 8, further comprising the steps of:

(f) bieving the compacts discharged from the compactor in step (b) prior to milling;

(g) collecting the uncompacted material from step (f); and (h) recycling the collected material back to the compactor.

11. The process of claim 9, wherein the excipient is selected from anhydrous lactose, low moisture microcrystalline cellulose or anhydrous calcium phosphate dibasic, and the first and second lubricants are each independently selected from magnesium stearate, sodium lauryl sulfate, sodium stearyl fumarate or hydrogenated vegetable oil.

12. The process of claim 11, wherein the excipient is anhydrous lactose and the first and second lubricants are both magnesium stearate.

13. The process of claim 11, wherein the capsule contains about 70 to 80% by weight indinavir sulfate, about 20 to 30% by weight anhydrous lactose and about 0.8% to 1.5% by weight magnesium stearate.

14. The process of claim 13, wherein the capsule contains about 75 to 78% by weight indinavir sulfate, about 22 to 25% by weight anhydrous lactose and about 0.9% to 1.1% by weight magnesium stearate.

15. The process of claim 14, comprising the steps of:

(a) mixing about 76% by weight indinavir sulfate, with about 23% by weight anhydrous lactose and about 0.5% by weight magnesium stearate;

(b) compacting the mix from step (a) in a roller compactor to form compacts;

(c) milling the compacts from step (b) to form granules;

(d) lubricating the granules from step (c) with about 0.5% by weight magnesium stearate; and (e) encapsulating the lubricated granules from step (d) to form the capsule.

16. The process of claim 9, comprising the steps of:

(a) mixing about 70 to 80% by weight indinavir sulfate with about 20 to 30% by weight of the excipient and about 0.4 to 0.75% by weight of the first lubricant in a ribbon mixer for approximately ten minutes at 20 rpm;

(b) compacting the mix from step (a) in a roller compactor at four to ten tons force to form compacts;

(c) milling the compacts from step (b) using a 0.062 inch screen at a speed of 2000 to 2500 rpm to form granules;

(d) lubricating the granules from step (c) with about 0.4 to 0.75% by weight of the second lubricant; and (e) encapsulating the lubricated granules from step (d) to form the capsule.

17. The process of claim 16, wherein the excipient is anhydrous lactose, and the first and second lubricants are magnesium stearate.

18. The process of claim 17, comprising the steps of:
(a) mixing about 75 to 78% by weight indinavir sulfate with about 22 to 25% by weight anhydrous lactose and about 0.45 to 0.55% by weight magnesium stearate in a ten cubic foot ribbon mixer for approximately ten minutes at 20 rpm for a total of approximately 200 revolutions;
(b) compacting the mix from step (a) in a roller compactor at four to ten tons force at a speed of 7 to 15 rpm and a feed speed of 10 to 60 rpm to form compacts;
(c) milling the compacts from step (b) in a CoMil® using a 0.062 inch screen at a speed of 2000 to 2500 rpm to form granules;
(d) lubricating the granules from step (c) with about 0.45 to 0.55% by weight magnesium stearate in a ten cubic foot ribbon mixer for approximately five minutes at 20 rpm for a total of approximately 100 revolutions; and
(e) encapsulating the lubricated granules from step (d) in a Bosch GKF encapsulation machine to form the capsule.

19. A pharmaceutical composition made by the process of claim 8.

* * * * *